(12) United States Patent
Peng et al.

(10) Patent No.: US 8,129,568 B2
(45) Date of Patent: Mar. 6, 2012

(54) FLUOROALKYL PHOSPHATE COMPOSITIONS

(75) Inventors: Sheng Peng, Hockessin, DE (US); Stephen James Getty, Wilmington, DE (US); Xianjun Meng, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/093,446

(22) Filed: Apr. 25, 2011

(65) Prior Publication Data

US 2011/0200815 A1  Aug. 18, 2011

Related U.S. Application Data

(62) Division of application No. 11/598,466, filed on Nov. 13, 2006, now Pat. No. 7,470,818.

(51) Int. Cl.
*C08F 9/29* (2006.01)

(52) U.S. Cl. ............... 568/8; 435/1.1; 514/52; 514/75; 524/589; 568/11

(58) Field of Classification Search ............... 568/8, 11; 514/52, 75; 435/1.1; 524/589
See application file for complete search history.

(56) References Cited

U.S. PATENT DOCUMENTS

| | | | |
|---|---|---|---|
| 3,083,224 A * | 3/1963 | Brace et al. ............. | 558/204 |
| 3,927,126 A | 12/1975 | Huber-Emden | |
| 3,979,469 A | 9/1976 | Jager | |
| 4,587,366 A | 5/1986 | von Werner | |
| 5,459,212 A | 10/1995 | Krespan et al. | |
| 5,481,028 A * | 1/1996 | Petrov et al. ............. | 560/184 |
| 5,491,261 A * | 2/1996 | Haniff et al. ............. | 562/582 |
| 6,025,521 A | 2/2000 | Krespan et al. | |
| 6,184,187 B1 | 2/2001 | Howell et al. | |
| 6,271,289 B1 * | 8/2001 | Longoria et al. ......... | 524/133 |
| 7,470,818 B2 * | 12/2008 | Peng et al. ............... | 568/8 |
| 2006/0047032 A1 | 3/2006 | Miller et al. | |
| 2006/0047044 A1 | 3/2006 | Miller et al. | |

FOREIGN PATENT DOCUMENTS

| | | |
|---|---|---|
| JP | 19988251348 A | 9/1998 |
| WO | WO 95/11877 | 5/1995 |
| WO | WO-95/11877 * | 5/1995 |
| WO | WO 01/36526 A1 | 5/2001 |
| WO | WO-01-36526 A1 * | 5/2001 |
| WO | WO 2006/116222 A2 | 11/2006 |

OTHER PUBLICATIONS

Balague et al., Synthesis of flourine telomers, Part 1. Telomerization of vinyldene flouride with perfluoroakl iodides: J. of Fluorine Chemistry, 1995, 70 (2) 215-223.
Duc et al., Radical telomerisation of vinylidene fluoride with diethyl hydrogenphosphonate, Characterisation of the first telomeric adducts and assessment of the transfer constants, J. of Fluorine Chemistry, 2001, 112 (1), 3-12.
Honda et al., Molecular aggregation structure and surface properties of poly(fluorcalkyl acrylate) thin films: Macromolecules, 2005, 38, 5699-5705.
Balague et al., Controlled step-wise telomerization of vinylidene fluoride, hexafluoropropene and trifluoroethylene with iodoflurinated transfer agents; J. of Fluorine Chemistry 102 (2000) 253-268, Elsevier Science S.A.

* cited by examiner

*Primary Examiner* — Peter D. Mulcahy
*Assistant Examiner* — Henry Hu

(57) ABSTRACT

A composition comprising a compound of formula (I) or (II):

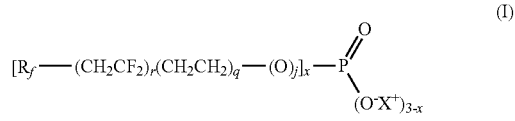

wherein
r and q are independently integers of 1 to 3;
$R_f$ is linear or branched chain perfluoroalkyl group having 1 to 6 carbon atoms;
j is an integer 0 or 1, or a mixture thereof,
x is 1 or 2,
Z is —O— or —S—,
X is hydrogen or M, and
M is an ammonium ion, an alkali metal ion, or an alkanolammonium ion is disclosed.

9 Claims, No Drawings

FLUOROALKYL PHOSPHATE COMPOSITIONS

FIELD OF INVENTION

This invention relates to the field of polyfluorinated compounds containing a vinylidene fluoride telomer linkage within the polyfluorinated chain, and particularly to such fluorophosphates, and to their use as surfactants, additives for coatings or treatment agents to impart water, oil and grease repellency to substrates such as paper, wood, ceramics, tile, cement or stone.

BACKGROUND

Polyfluorinated compositions are used in the preparation of a wide variety of surface treatment materials. These polyfluorinated compositions are typically made of perfluorinated carbon chains connected directly or indirectly to nonfluorinated functional groups capable of further reaction such as hydroxyl groups, carboxylic acid groups, halide groups and others. Various materials made from perfluorinated compositions are known to be useful as surfactants or treating agents to provide surface effects to substrates. Surface effects include repellency to moisture, soil, and stains, and other effects, which are particularly useful for fibrous substrates and other substrates such as hard surfaces. Many such surfactants and treating agents are fluorinated polymers or copolymers.

Most commercially available fluorinated polymers useful as treating agents for imparting surface effects to substrates contain predominantly eight or more carbons in the perfluoroalkyl chain to provide the desired properties. Honda et al, in Macromolecules, 2005, 38, 5699-5705 teach that for perfluoroalkyl chains of greater than 8 carbons, orientation of the perfluoroalkyl groups, designated $R_f$ groups, is maintained in a parallel configuration while for such chains having less than 6 carbons, reorientation occurs. This reorientation decreases surface properties such as contact angle. Thus, polymers containing shorter chain perfluoroalkyls have traditionally not been successful commercially.

EP 1 238 004 (Longoria et al.) discloses a mixture of a fluoroalkyl phosphates and a fluoroacrylate polymer for use in providing stain resistance to stone, masonry, and other hard surfaces.

It is desirable to improve particular surface effects and to increase the fluorine efficiency; i.e., boost the efficiency or performance of treating agents so that lesser amounts of the expensive fluorinated compositions are required to achieve the same level of performance, or so that better performance is achieved using the same level of fluorine. It is desirable to reduce the chain length of the perfluoroalkyl groups thereby reducing the amount of fluorine present, while still achieving the same or superior surface effects.

There is a need for compositions that significantly improve the repellency and stain resistance of fluorinated treating agents for substrates while using lower levels of fluorine. There is also a need for compositions useful as additives in coatings, such as paints, stains, or clear coats, to provide resistance to blocking and enhanced open time extension. The present invention provides such compositions.

SUMMARY OF INVENTION

One embodiment of the invention is a composition comprising one or more compounds of formula (I) or (II):

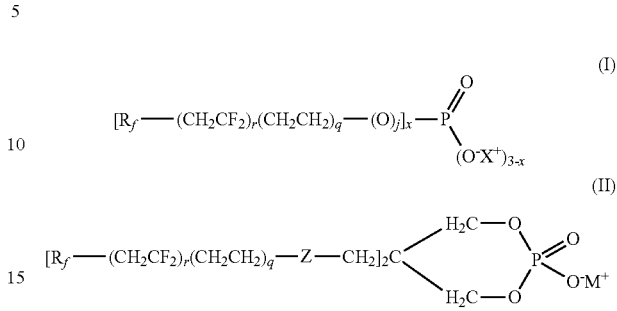

wherein
r and q are independently integers of 1 to 3;
$R_f$ is linear or branched chain perfluoroalkyl group having 1 to 6 carbon atoms;
j is an integer 0 or 1, or a mixture thereof,
x is 1 or 2,
Z is —O— or —S—,
X is hydrogen or M, and
M is an ammonium ion, an alkali metal ion, or an alkanolammonium ion.

Another aspect of the invention is a method of providing water repellency, oil repellency and stain resistance to a substrate comprising contacting the substrate with a composition comprising one or more compounds of formula (I) or (II).

Another aspect of the invention is a method of providing resistance to blocking, open time extension and oil repellency to a substrate having deposited thereon a coating composition comprising adding to the coating composition, prior to deposition on the substrate, a composition comprising one or more compounds of formula (I) or (II).

Another embodiment of the invention is a substrate to which has been applied a composition of comprising one or more compounds of formula (I) or (II).

DETAILED DESCRIPTION OF INVENTION

Hereinafter trademarks are designated by upper case.

The present invention comprises fluorinated aqueous compositions that, when applied to substrate surfaces, provide improved oil repellency, water repellency and stain resistance, and the process for treating such substrates with the compositions of this invention. The compositions of the present invention are also useful as additions to coating compositions to impart certain surface properties to substrates coated with such compositions. Other embodiments of the invention include substrates having improved surface properties such as oil repellency and stain repellency.

Fluorinated compounds of formula (I) and (II) described above useful in various embodiments of the invention are available by synthesis according to the following scheme:

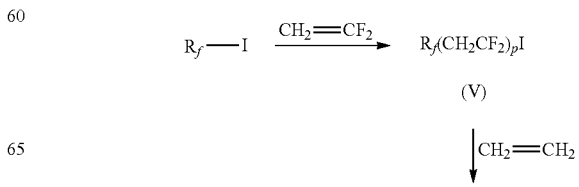

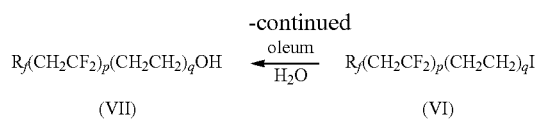

The telomerization of vinylidene fluoride (VDF) with linear or branched perfluoroalkyl iodides is well known, and produces compounds of the structure $R_f(CH_2CF_2)_pI$, wherein, p is 1 to 3 or more and $R_f$ is a C1 to C6 perfluoroalkyl group. For example, see Balague, et al, "Synthesis of fluorinated telomers, Part 1, Telomerization of vinylidene fluoride with perfluoroalkyl iodides", J. Flour Chem. (1995), 70(2), 215-23. The specific telomer iodides (V) are isolated by fractional distillation. The telomer iodides (V) can be treated with ethylene by procedures described in U.S. Pat. No. 3,979,469, (Ciba-Geigy, 1976) to provide the telomer ethylene iodides (VI) wherein q is 1 to 3 or more. The telomer ethylene iodides (VI) can be treated with oleum and hydrolyzed to provide the corresponding telomer alcohols (VII) according to procedures disclosed in WO 95/11877 (Elf Atochem S.A.). The higher homologs (q=2, 3) of telomer ethylene iodides (VI) are available with excess ethylene at high pressure. The telomer ethylene iodides (VI) can be treated with a variety of reagents to provide the corresponding thiols according to procedures described in J. Fluorine Chemistry, 104, 2 173-183 (2000). One example is the reaction of the telomer ethylene iodides (VI) with sodium thioacetate, followed by hydrolysis.

Specific fluorinated telomer alcohols derived from telomerization of vinylidene fluoride and ethylene and useful in the invention are listed in Table 1A.

TABLE 1A

| Compound No. | Structure |
|---|---|
| 1. | $C_2F_5CH_2CF_2CH_2CH_2OH$, |
| 2. | $C_2F_5(CH_2CF_2)_2CH_2CH_2OH$, |
| 3. | $C_2F_5(CH_2CF_2)_3CH_2CH_2OH$, |
| 4. | $C_2F_5CH_2CF_2(CH_2CH_2)_2OH$, |
| 5. | $C_2F_5(CH_2CF_2)_2(CH_2CH_2)_2OH$, |
| 6. | $C_4F_9CH_2CF_2CH_2CH_2OH$, |
| 7. | $C_4F_9(CH_2CF_2)_2CH_2CH_2OH$, |
| 8. | $C_4F_9(CH_2CF_2)_3CH_2CH_2OH$, |
| 9. | $C_4F_9CH_2CF_2(CH_2CH_2)_2OH$, |
| 10. | $C_4F_9(CH_2CF_2)_2(CH_2CH_2)_2OH$, |
| 11. | $C_6F_{13}CH_2CF_2CH_2CH_2OH$, |
| 12. | $C_6F_{13}(CH_2CF_2)_2CH_2CH_2OH$, |
| 13. | $C_6F_{13}(CH_2CF_2)_3CH_2CH_2OH$, |
| 14. | $C_6F_{13}CH_2CF_2(CH_2CH_2)_2OH$, |
| 15. | $C_6F_{13}(CH_2CF_2)_2(CH_2CH_2)_2OH$. |

Specific fluoroether thiols useful in forming compounds of the invention include those listed in Table 1B.

TABLE 1B

| Compound No. | Structure |
|---|---|
| 21. | $C_2F_5CH_2CF_2CH_2CH_2SH$, |
| 22. | $C_2F_5(CH_2CF_2)_2CH_2CH_2SH$, |
| 23. | $C_2F_5(CH_2CF_2)_3CH_2CH_2SH$, |
| 24. | $C_4F_9CH_2CF_2CH_2CH_2SH$, |
| 25. | $C_4F_9(CH_2CF_2)_2CH_2CH_2SH$, |
| 26. | $C_4F_9(CH_2CF_2)_3CH_2CH_2SH$, |
| 27. | $C_6F_{13}CH_2CF_2CH_2CH_2SH$, |
| 28. | $C_6F_{13}(CH_2CF_2)_2CH_2CH_2SH$, |
| 29. | $C_6F_{13}(CH_2CF_2)_3CH_2CH_2SH$. |

The fluoroalkylphosphates of formula (I) and (II) are prepared according to the method described by Longoria et al in U.S. Pat. No. 6,271,289, and Brace and Mackenzie, in U.S. Pat. No. 3,083,224, each herein incorporated by reference. Typically, either phosphorus pentoxide ($P_2O_5$) or phosphorus oxychloride ($POCl_3$) is reacted with the fluoroalkyl alcohol or fluoroalkyl thiol to give mixtures of the mono- and bis(fluoroalkyl)phosphoric acids. Neutralization, using common bases such as ammonium or sodium hydroxides, or alkanol amines, for instance, diethanolamine (DEA), provides the corresponding phosphates. Reacting an excess of fluoroalkyl alcohol or fluoroalkyl thiol with $P_2O_5$ followed by neutralization provides a mixture of mono(fluoroalkyl)phosphate and bis(fluoroalkyl)phosphate. Higher ratios of bis(fluoroalkyl) phosphate to mono(fluoroalkyl)phosphate are obtained by using the method of Hayashi and Kawakami in U.S. Pat. No. 4,145,382. The phosphite and phosphinate compositions are prepared in a similar manner.

The resulting composition is then diluted with water, mixture of water and solvent, or further dispersed or dissolved in a solvent selected from the groups comprising simple alcohols and ketones that are suitable as the solvent for final application to substrates (hereinafter the "application solvent"). Alternatively, an aqueous dispersion, made by conventional methods with surfactants, is prepared by removing solvents by evaporation and the use of emulsification or homogenization procedures known to those skilled in the art. Such solvent-free emulsions may be preferred to minimize flammability and volatile organic compounds (VOC) concerns. The final product for application to a substrate can be a dispersion, if water based, or a solution.

It will be apparent to one skilled in the art that many changes to any or all of the procedures described above may also be used to optimize the reaction conditions for obtaining maximum yield, productivity or product quality.

The present invention comprises fluorinated aqueous mixtures comprising a mixture of an anionic aqueous fluoroalkyl phosphate, phosphite or phosphonite acid solution neutralized with a base, preferably an amine such as dialkanolamine base. The composition is neutralized to a pH of about 5 to about 10, preferably about 6 to about 9 and most preferably, from about 6 to about 8.

The various molar ratios of the fluoroalcohol or fluorothiol, acid, and base can be identified by the format (a:1:b): thus the (2:1:1) salt is, for example, the bis(fluoroalkyl) phosphate amine salt, the (1:1:2) salt is, for example, the fluoroalkyl phosphate bis(amine salt) and the (1:1:1) salt is, for example, the fluoroalkyl phosphate amine salt. Preferably the (2:1:1) salt is the bis(fluoroalkyl) phosphate diethanolamine salt, the (1:1:2) salt is the fluoroalkyl phosphate bis(diethanolamine salt) and the (1:1:1) salt is the fluoroalkyl phosphate diethanolamine salt.

Preferred embodiments of the invention are compositions of formula (I) or (II) wherein $R_f$ has 4 to 6 carbon atoms, and r, q and j are each =1. Other preferred embodiments are compositions wherein M is an ammonium or an alkanolammonium ion. Other preferred compositions of the invention comprise a mono(fluoroalkyl) phosphate of formula (I), wherein x=1 of about 15 to 80 mol %, and a bis(fluoroalkyl) phosphate of formula (I) wherein x=2 of about 20 to about 85 mol %. These preferred compositions are useful and preferred in all other embodiments of the invention, including methods of application, and treated substrates, discussed herein.

The salts of the fluoroalkylphosphates are preferred over the corresponding acids as outlined in U.S. Pat. No. 3,083,224 by reason of their increased water solubility.

The present invention further comprises a method of providing water repellency, oil repellency, and stain resistance to a substrate comprising contacting the substrate with a composition of formula (I) or (II) as defined above, or a mixture thereof. The composition of the present invention is typically applied by contacting the substrate with the composition by conventional means, including, but not limited to, brush, spray, roller, doctor blade, wipe, immersion, dip techniques, foam, liquid injection, and casting. Optionally, more than one coat can be used, particularly on porous surfaces.

The compositions of the present invention can be used as an additive during the manufacture of substrates. They can be added at any suitable point during manufacture. For example, in the case of paper, they can be added to the paper pulp in a size press. Preferably, about 0.3 weight % to about 0.5 weight % of the composition of the invention is added to paper pulp, based on the dry solids of the composition and dry paper fiber.

When used as a surface treatment for paper, the compositions of the invention are typically diluted with water to give an application solution having about 0.01 weight % to about 20 weight %, preferably about 0.1 weight % to about 10 weight %, and most preferably about 0.5 weight % to about 5 weight %, of the composition based on solids. The coverage as applied to paper is about 10 $g/m^2$ to about 200 $g/m^2$, and preferably about 10 $g/m^2$ to about 100 $g/m^2$ of the application solution. Preferably the application results in about 0.1 $g/m^2$ to about 5.0 $g/m^2$ of solids being applied to the paper.

When used on stone, tile and other hard surfaces, the compositions of the invention are typically diluted with water to give an application solution having about 0.1 weight % to about 20 weight %, preferably from about 1.0 weight % to about 10 weight %, and most preferably from about 2.0 weight % to about 5.0 weight %, of the composition based on solids. The coverage as applied to a substrate is about 100 g of application solution per sq meter ($g/m^2$) for semi-porous substrates (e.g. limestone) and 200 $g/m^2$ for porous substrates (e.g. Saltillo). Preferably the application results in about 0.1 $g/m^2$ to about 2.0 $g/m^2$ of solids being applied to the surface.

The composition of this invention is applied to or contacted with the substrate as such, or in combination with one or more other finishes or surface treating agents. The composition of the present invention optionally further comprises additional components such as treating agents or finishes to achieve additional surface effects, or additives commonly used with such agents or finishes. Such additional components comprise compounds or compositions that provide surface effects such as stain repellency, stain release, soil repellency, soil release, water repellency, oil repellency, antimicrobial protection, and similar effects. One or more of such treating agents or finishes can be blended with the composition of the present invention and applied to the substrate.

Other additives commonly used with such treating agents or finishes can also be present such as surfactants, pH adjusters, leveling agents, wetting agents, and other additives known by those skilled in the art. Examples of such finishes or agents include processing aids, foaming agents, lubricants, anti-stains, and the like. The composition is applied at a manufacturing facility, retailer location, or prior to installation and use, or at a consumer location.

The present invention further comprises a method of providing resistance to blocking, open time extension, and oil repellency to a substrate having deposited thereon a coating composition comprising adding to the coating composition prior to deposition on the substrate a composition of the above formula (I) or (II) or mixtures thereof. Suitable coating compositions, referred to herein by the term "coating base", include a composition, typically a liquid formulation, of an alkyd coating, Type I urethane coating, unsaturated polyester coating, or water-dispersed coating, and is applied to a substrate for the purpose of creating a lasting film on the substrate surface. These are conventional paints, stains, and similar coating compositions.

By the term "alkyd coating" as used herein is meant a conventional liquid coating based on alkyd resins, typically a paint, clear coating, or stain. The alkyd resins are complex branched and cross-linked polyesters containing unsaturated aliphatic acid residues. Conventional alkyd coatings utilize, as the binder or film-forming component, a curing or drying alkyd resin. Alkyd resin coatings contain unsaturated aliphatic acid residues derived from drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Such drying oils have been used as raw materials for oil-based coatings and are described in the literature.

By the term "urethane coating" as used hereinafter is meant a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. Urethane coatings are classified by ASTM D-1 into five categories. Type I urethane coatings contain a pre-reacted autoxidizable binder as described in Surface Coatings Vol. I, previously cited. These are also known as uralkyds, urethane-modified alkyds, oil-modified urethanes, urethane oils, or urethane alkyds, are the largest volume category of polyurethane coatings and include paints, clear coatings, or stains. The cured coating is formed by air oxidation and polymerization of the unsaturated drying oil residue in the binder.

By the term "unsaturated polyester coating" as used hereinafter is meant a conventional liquid coating based on unsaturated polyester resins, dissolved in monomers and containing initiators and catalysts as needed, typically as a paint, clear coating, or gel coat formulation. Unsaturated polyester resins contain as the unsaturated prepolymer the product obtained from the condensation polymerization of a glycol such as 1,2-propylene glycol or 1,3-butylene glycol with an unsaturated acid such as maleic (or of maleic and a saturated acid, e.g., phthalic) in the anhydride form. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. In order that curing can take place at room temperature, the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing using, for instance, ultraviolet light. This form of cure, in which no heat is produced, is particularly suited to films on wood or board. Other radiation sources, for instance electron-beam curing, are also used.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as well as members of other classifications. Water-dispersed coatings general contain other common coating ingredients. Water-dispersed coatings are exemplified by, but not limited to, pigmented coatings such as latex paints, unpigmented coatings such as wood sealers, stains, and finishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

Blocking is the undesirable sticking together of two coated surfaces when pressed together, or placed in contact with each other for an extended period of time. When blocking occurs separation of the surfaces can result in disruption of the coating on one or both surfaces. Thus improved resistance to blocking is beneficial in many situations where two coated surfaces need to be in contact, for example on window frames.

The term "open time extension" is used herein to mean the time during which a layer of liquid coating composition can be blended into an adjacent layer of liquid coating composition without showing a lap mark, brush mark, or other application mark. It is also called wet-edge time. Latex paint containing low boiling, volatile organic chemicals (VOC) has shorter than desired open-time due to lack of high boiling temperature VOC solvents. Lack of open time extension will cause surface defects such as overlapping brush marks or other marks. A longer open time extension is beneficial when the appearance of the coated surface is important, as it permits application of the coating without leaving overlap marks, brush marks, or other application marks at the area of overlap between one layer of the coating and an adjacent layer of the coating.

When used as additives the compositions of the present invention are effectively introduced to the coating base or other composition by thoroughly stirring it in at room or ambient temperature. More elaborate mixing can be employed such as using a mechanical shaker or providing heat or other methods. Such methods are not necessary and do not substantially improve the final composition. When used as an additive to latex paints, the compositions of the invention generally are added at about 0.001 weight % to about 5 weight % by dry weight of the composition of the invention in the wet paint. Preferably about 0.01 weight % to about 1 weight %, and more preferably 0.1 weight % to about 0.5 weight % is used.

The present invention also comprises substrates treated with the composition of the present invention. Suitable substrates include fibrous and hard surface substrates. The fibrous substrates include wood, paper, and leather. The hard surface substrates include porous and non-porous mineral surfaces, such as glass, stone, masonry, concrete, unglazed tile, brick, porous clay and various other substrates with surface porosity. Specific examples of such substrates include unglazed concrete, brick, tile, stone including granite, limestone and marble, grout, mortar, statuary, monuments, wood, composite materials such as terrazzo, and wall and ceiling panels including those fabricated with gypsum board. These are used in the construction of buildings, roads, parking ramps, driveways, floorings, fireplaces, fireplace hearths, counter tops, and other decorative uses in interior and exterior applications.

The compositions of the present invention are useful to provide one or more of excellent water repellency, oil repellency, and stain resistance to treated substrates. They also are useful to provide resistance to blocking, open time extension, and oil repellency to substrates coated with a coating composition to which the compositions of the present invention have been added. These properties are obtained using lower fluorine concentrations compared with conventional perfluorocarbon surface treatment agents, providing improved "fluorine efficiency" in the protection of treated surfaces The compositions of the present invention are effective at fluorine concentrations about one half to one third of the fluorine concentration for conventional fluorochemical surface protectants. The compositions of the present invention also allow for the use of shorter fluoroalkyl groups containing 6 or fewer fluorinated carbon atoms while conventional commercially available surface treatment products typically show poor oil repellency and water repellency performance if the fluoroalkyl groups contain less 8 carbon atoms.

Materials and Test Methods

The following materials and test methods were used in the examples herein. The groups $C_3F_7$, $C_4F_9$, and $C_6F_{13}$, referred to in the list of specific alcohols and thiols in Tables 1A and 1B, and in the examples herein, refer to linear perfluoroalkyl groups unless specifically indicated otherwise. Compound numbers refer to the list of alcohols in Table 1A.

Compound 6

Ethylene (25 g) was introduced to an autoclave charged with $C_4F_9CH_2CF_2I$ (217 g) and d-(+)-limonene (1 g), and the reactor heated at 240° C. for 12 h. The product was isolated by vacuum distillation to provide $C_4F_9CH_2CF_2CH_2CH_2I$.

Fuming sulfuric acid (70 mL) was added slowly to 50 g of $C_4F_9CH_2CF_2CH_2CH_2I$ and mixture stirred at 60° C. for 1.5 h. The reaction was quenched with ice-cold 1.5 wt % $Na_2SO_3$ aqueous solution and heated at 95° C. for 0.5 h. The bottom layer was separated and washed with 10 wt % aqueous sodium acetate, and distilled to provide compound 6: bp 54~57° C. at 2 mmHg (267 Pascals).

Compound 7 Ethylene (18 g) was introduced to an autoclave charged with $C_4F_9(CH_2CF_2)_2I$ (181 g) and d-(+)-limonene (1 g), and the reactor heated at 240° C. for 12 h. The product was distilled to provide $C_4F_9(CH_2CF_2)$ $2CH_2CH_2I$.

$C_4F_9(CH_2CF_2)_2CH_2CH_2I$ (10 g) and N-methylformamide (8.9 mL) were heated to 150° C. for 26 h. The reaction was cooled to 100° C., followed by the addition of water to separate the crude ester. Ethyl alcohol (3 mL) and p-toluene sulfonic acid (0.09 g) were added to the crude ester, and the reaction was stirred at 70° C. for 15 min. Then ethyl formate and ethyl alcohol were distilled out to give a crude product. The crude alcohol was dissolved in ether, washed with aqueous sodium sulfite, water, and brine in series, and dried over magnesium sulfate. The product was distilled to give compound 7: bp 90~94° C. at 2 mmHg (257 Pascals).

Compound 11

Ethylene (15 g) was introduced to an autoclave charged with $C_6F_{13}CH_2CF_2I$ (170 g) and d-(+)-limonene (1 g), and then the reactor was heated at 240° C. for 12 h. Product was isolated by vacuum distillation to provide $C_6F_{13}CH_2CF_2CH_2CH_2I$.

Fuming sulfuric acid (129 mL) was added slowly to $C_6F_{13}CH_2CF_2CH_2CH_2I$ (112 g). The mixture was stirred at 60° C. for 1.5 h. Then the reaction was quenched with ice-cold 1.5 wt % aqueous $Na_2SO_3$ and heated at 95° C. for 0.5 h. The bottom layer was separated and washed with 10% sodium acetate aqueous solution and distilled to provide compound 11: mp 38° C.

Compound 12

Ethylene (56 g) was introduced to an autoclave charged with $C_6F_{13}(CH_2CF_2)_2I$ (714 g) and d-(+)-limonene (3.2 g), and the reactor heated at 240° C. for 12 h. Product was isolated by vacuum distillation to provide $C_6F_{13}(CH_2CF_2)_2CH_2CH_2I.C_6F_{13}(CH_2CF_2)_2CH_2CH_2I$ (111 g) and N-methyl-formamide (81 mL) were heated to 150° C. for 26 h. The reaction was cooled to 100° C., followed by the addition of water to separate the crude ester. Ethyl alcohol (21 mL) and p-toluene sulfonic acid (0.7 g) were added to the crude ester, and the reaction was stirred at 70° C. for 15 min. Then ethyl formate and ethyl alcohol were distilled out to give a crude alcohol. The crude alcohol was dissolved in ether, washed with aqueous sodium sulfite, water, and brine in turn, and then dried over magnesium sulfate. The product was distilled under vacuum to provide compound 12: mp 42° C.

Test Method 1—Repellency for Paper

The oil repellency of paper was tested by using the AATCC Kit Test Procedure (118-1997). Each test specimen was placed on a clean flat surface, test side up, being careful not to touch the area to be tested. From a height of about one inch (2.5 cm), a drop of test solution from an intermediate Kit Number testing bottle was dropped onto the test area. A stopwatch was started as the drop was applied. After exactly 15 seconds, the excess fluid was removed with a clean swatch of cotton tissue and the wetted area was immediately examined. Failure was evidenced by a pronounced darkening of the specimen caused by penetration, even in a small area, under the drop. The procedure was repeated as required, making sure that drops from other Kit Number bottles fell in untouched areas. The Results were reported as the Kit Rating, which was the highest numbered solution that stood on the surface of the specimen for 15 seconds without causing failure. The average Kit Rating of five specimens to the nearest 0.5 integer was reported.

TABLE 2A

The composition of AATCC Kit test solution (Tappi Kit Test Solution)

| Rating No. | Composition Results |
|---|---|
| 0 | The test sample fails Kaydol[a] |
| 1 | Passes Kaydol |
| 2 | Passes 65:35 (v/v) Kaydol:n-hexadecane |
| 3 | Passes n-hexadecane |
| 4 | Passes n-tetradecane |
| 5 | Passes n-dodecane |
| 6 | Passes n-decane |
| 7 | Passes n-octane |
| 8 | Passes n-heptane |

[a]Kaydol (CAS # 8020-83-5) is a light mineral oil available from Pfaltz & Bauer, Waterbury, CT, USA.

Test Method 2—Blocking Resistance of Architectural Latex Paints

The test method described herein is a modification of ASTM D4946-89—Standard Test Method for Blocking Resistance of Architectural Paints, which is hereby specifically incorporated by reference.

The face-to-face blocking resistance of paints to be tested was evaluated in this test. Blocking, for the purpose of this test, is defined as the undesirable sticking together of two painted surfaces when pressed together or placed in contact with each other for an extended period of time.

The paint to be tested was cast on a polyester test panel using the applicator blade. All painted panels should be protected from grease, oil, fingerprints, dust, et cetera; surface contamination will affect blocking resistance results. Typically, results are sought at 24 hours after casting the paint. After the panels have been conditioned in the conditioned room as specified in the test method for the desired period of time, six squares (3.8 cm×3.8 cm) were cut out from the painted test panel. The cut sections (three pairs) were placed with the paint surfaces face-to-face for each of the paints to be tested. Place the cut sections (three pairs) with the paint surfaces face-to-face for each of the paints to be tested. The face-to-face specimens were in the 50° C. oven on the marble tray. A no. 8 stopper was placed on top, with the smaller diameter in contact with the specimens, and then a 1000 g weight was placed on top of the stopper. This resulted in a pressure of 1.8 psi (12,400 Pascal) on the specimens. One weight and stopper was be used for each specimen to be tested. After exactly 30 minutes, the stoppers and weights were taken off the test specimens which were removed from the oven and allowed to cool in the conditioned room for 30 minutes before determining the block resistance.

After cooling, the specimens were separated by peeling apart with a slow and steady force. The blocking resistance was rated from 0 to 10, corresponding to a subjective tack assessment (sound made upon separation of the painted specimens) or seal (complete adhesion of the two painted surfaces) as determined by the operator of the method. The specimen was put near the ear to actually hear the degree of tack. The rating system is described in Table 2B. The degree of seal was estimated from the appearance of the specimens and the fraction of the paint surfaces that adhere. Paint tearing away from the test panel backing was an indication of seal. A higher number indicates better resistance to blocking.

TABLE 2B

Blocking Resistance Numerical Ratings

| Blocking Resistance Numerical Ratings | Description of the Separation | Performance Description |
|---|---|---|
| 10 | no tack | perfect |
| 9 | trace tack | excellent |
| 8 | very slight tack | very good |
| 7 | slight tack | good/very good |
| 6 | moderate to slight tack | good |
| 5 | moderate tack | fair |
| 4 | very tacky - no seal | poor to fair |
| 3 | 5 to 25% seal | poor |
| 2 | 25 to 50% seal | poor |
| 1 | 50 to 75% seal | very poor |
| 0 | 75 to 100% seal | very poor |

Test Method 3—Surface Tension Measurement

Surface tension is measured using a Kruess Tensiometer, K11 Version 2.501 in accordance with the equipment instructions. The Wilhelmy Plate method is used. A vertical plate of known perimeter is attached to a balance, and the force due to wetting is measured. 10 replicates are tested of each dilution, and the following machine settings are used:

Method: Plate Method SFT
Interval: 1.0 s
Wetted length: 40.2 mm
Reading limit: 10
Min Standard Deviation: 2 dynes/cm
Gr. Acc.: 9.80665 m/s^2

Test Method 4—Contact Angle Measurement

Contact angles are measured by the Sessile Drop Method, which is described by A. W. Adamson in The Physical Chemistry of Surfaces, Fifth Edition, Wiley & Sons, New York, N.Y., 1990. Additional information on the equipment and procedure for measuring contact angles is provided by R. H. Dettre et al. in "Wettability", Ed. by J. C. Berg, Marcel Dekker, New York, N.Y., 1993.

In the Sessile Drop Method, a Ramè-Hart optical bench (available from Ramè-Hart Inc., 43 Bloomfield Ave., Mountain Lakes, N.J.) is used to hold the substrate in the horizontal position. The contact angle is measured at a prescribed temperature with a telescoping goniometer from the same manufacturer. A drop of test liquid is placed on a polyester scrub test panel (Leneta P-121 dull black or equivalent, Leneta Company, Mahwah, N.J.) and the tangent is precisely determined at the point of contact between the drop and the surface. An advancing angle is determined by increasing the size of the drop of liquid and a receding angle is determined by decreasing the size of the drop of liquid. The data are presented typically as advancing and receding contact angles.

The relationship between water and organic liquid contact angles, and the cleanability and dirt retention of surfaces is described by A. W. Adamson, cited above. In general, higher hexadecane contact angles indicate that a surface has greater dirt and soil repellency, and easier surface cleanability.

The water and hexadecane advancing angles of the dried coating compositions containing a composition of the present invention as an additive were measured on coatings cast on the Leneta panels, available from the Leneta Company, Mahwah, N.J. The control was the same coating composition with no composition of the present invention added.

Test Method 5—Open-Time Extension

Open-time is time during which a layer of applied liquid coating composition can be blended into an adjacent layer of liquid coating composition without showing a lapmark, brush mark, or other application mark. It is also called wet-edge time. Low VOC latex paint has shorter than desired open-time due to lack of high boiling temperature VOC solvents. Lack of sufficient open-time will result in overlapping brush marks or other marks. Open-time testing is conducted by a well-accepted industry practice, called thumb press method as described herein. A double strip drawdown panel of the control sample and the sample with 0.1% active ingredient of the sample to be tested is employed. The coating composition to be tested and the control are the same coating composition wherein the control contains no additive to be tested, and the sample to be tested contains a composition of the present invention as an additive. The panel is made with a 7 cm doctor blade at 20-25° C. and 40-60% relative humidity. A double thumb press with equal pressure is then applied to each sample side by side at 1-2 minute intervals. The end point is when no paint residue on the thumb is observed. The time from when the drawdown is made to the end point is recorded as open-time. The percent difference between the control and sample containing the additive is recorded as the percent open-time extension. Compositions of the present invention were tested in a semi-gloss latex paint.

Test Method 6—Determination of Water and Oil Repellency

This test method describes the procedure for testing water repellency on hard surface substrates including limestone and granite. Square tiles of 12 inch square (30.5 cm$^2$) of a limestone (Euro Beige) and granite (White Cashmere), were cut into 4 inch (10.2 cm) by 12 inch (30.5 cm) samples. After cutting, the samples were rinsed to remove any dust or dirt and allowed to dry thoroughly, typically for at least 24 hours. A penetrating solution was prepared by mixing a composition of the present invention with deionized water to provide a fluorine concentration of 0.8% fluorine by weight. A ½-inch (1.3 cm) paintbrush was used to apply the solution to samples of each substrate surface. The surface was then allowed to dry for fifteen minutes. If necessary, the surface was wiped with a cloth soaked in the treating solution to remove any excess. After the treated substrates dried overnight, three drops of deionized water and three drops of canola oil were placed on each substrate and allowed to sit for five minutes. Visual contact angle measurements were used to determine water and oil repellency. The following rating chart was used to determine contact angle using a 0 to 5 scale, as shown below:

Repellency Rating 5 (Excellent): Contact angle 100°-120°.
Repellency Rating 4 (Very good): Contact angle 75°-90°.
Repellency Rating 3 (Good): Contact angle 45°-75°.
Repellency Rating 2 (Fair): Contact angle 25°-45°.
Repellency Rating 1 (Poor): Contact angle 10°-25°.
Repellency Rating 0 (Penetration): Contact angle <10°.

Higher numbers indicate greater repellency with ratings of 2 to 5 being acceptable. The data is reported in the tables as water beading and oil beading.

Test Method 7—Determination of Stain Resistance

Stain resistance was determined on limestone granite substrates using this method. Square tiles of 12 inch square (30.5 cm$^2$) of a sample limestone (Euro Beige) and granite (White Cashmere), were cut into 4 inch (10.2 cm) by 12 inch (30.5 cm) samples. After cutting, the samples were rinsed to remove any dust or dirt and allowed to dry thoroughly, typically for at least 24 hours. A penetrating solution was prepared by mixing a composition of the present invention with deionized water to provide a fluorine concentration of 0.8% fluorine by weight. A ½-inch (1.3 cm) paintbrush was used to apply the solution to samples of each substrate surface. The surface was then allowed to dry for fifteen minutes. If necessary, the surface was wiped with a cloth soaked in the treating solution to remove any excess. After the treated substrates dried overnight, the following food stains were placed at intervals on the surface of the substrate: 1) hot bacon grease, 2) cola, 3) black coffee, 4) grape juice, 5) Italian salad dressing, 6) ketchup, 7) lemon juice, 8) mustard, 9) canola oil and 10) motor oil. After a 24-hour period, the food stains were blotted or lightly scraped from the substrate surface. The substrate's surface was rinsed with water and a 1% soap solution, and a stiff bristle brush was used to scrub the surface 10 cycles back and forth. The substrates were then rinsed with water and allowed to dry for 24 hours before rating.

The stains remaining on the tile surfaces after cleaning were rated visually according to a scale of 0 to 4 as follows: 0=no stain; 1=very light stain; 2=light stain; 3=moderate stain; and 4=heavy stain. The ratings for each substrate type are summed for each of the stains to give a composite rating for each type. The maximum total score for one substrate was 10 stains times the maximum score of 4=40. Lower scores indicated better stain protection, with scores of 20 or less being acceptable and with zero indicating the best protection with no stain present.

EXAMPLES

Example 1

Phosphorous pentoxide (1.44 g, 0.0102 mol) was added to Compound 6 (10 g, 0.03 mol, Table 1A) at 85° C. and the mixture heated to 100° C. for 16 h. Isopropyl alcohol (17.05 mL) was then added to the reaction mixture at 85° C. and stirred for 0.5 h, followed by the addition of deionized (DI) water (21.66 mL). After 1.5 h, diethanolamine (DEA, 3.0 mL, 0.031 mol) was added and the reaction was stirred for 2 h at 65° C. to provide a phosphate 1 of formula (I) wherein r, q and j=1, $R_f$=—$C_4F_9$, and $X^+$=$^+NH_2(CH_2CH_2OH)_2$.

Examples 2-4

Compounds 11, 7 and 12 (Table 1A) were treated in a similar manner as described in Example 1 to provide phosphate 2 (r, q and j=1, $R_f$=—$C_6F_{13}$), phosphate 3 (r=2, q and j=1, $R_f$=—$C_4F_9$) and phosphate 4 (r=2, q and j=1, $R_f$=—$C_6F_{13}$), respectively, wherein for each $X^+$=$^+NH_2(CH_2CH_2OH)_2$.

Comparative Example A

The procedure of Example 1 was employed, but using the same equivalents of a perfluoroalkylethyl alcohol mixture of the formula $F(CF_2)_aCH_2CH_2OH$, with an average molecular weight of 471 wherein a ranged from 6 to 14, and was predominately 6, 8, and 10. The typical mixture was as follows: 27% to 37% of a=6, 28% to 32% of a=8, 14% to 20% of a=10, 8% to 13% of a=12 and 3% to 6% of a=14.

Example Testing

Products from Examples 1 to 4 and Comparative Example A were diluted to equal weight % solids and applied to paper by padding the paper samples. After drying the paper samples were tested for oil repellency using Test Method 1. The paper used in the test was white paper (bleached 50# paper). Results are in Table 3.

TABLE 3

Oil Repellency on Paper

| Example | Phosphate g/m² | Fluorine g/m² | Repellency |
| --- | --- | --- | --- |
| Untreated control | 0 | 0 | 0 |
| 1 | 0.2929 | 0.138 | 3 |
| 2 | 0.2929 | 0.151 | 5 |
| 3 | 0.2929 | 0.141 | 3 |
| 4 | 0.2929 | 0.158 | 4 |
| Comparative A | 0.2929 | 0.154 | 4 |
| 1 | 0.5859 | 0.275 | 5 |
| 2 | 0.5859 | 0.303 | 6 |
| 3 | 0.5859 | 0.281 | 5 |
| 4 | 0.5859 | 0.316 | 6 |
| Comparative A | 0.5859 | 0.308 | 5 |

These results demonstrated that the above examples provided excellent oil repellency when applied to a paper substrate, and are comparable or, in some cases, superior to a comparative example having a perfluoroalkyl group containing six to eight carbon atoms which do not contain a vinylidene fluoride telomer linkage.

The product of Example 4 was applied to limestone and granite and tested for water repellency and oil repellency using Test Method 6, and was tested for stain resistance using Test Method 7. Results are in Tables 4 and 5.

TABLE 4

Stain resistance, water and oil repellency for limestone[a]

| Food stains | Example 4 | Control |
| --- | --- | --- |
| Cola | 1 | 2 |
| Mustard | 1 | 4 |
| Ketchup | 0 | 2 |
| Grape juice | 2 | 4 |
| Italian dressing | 1 | 4 |
| Coffee | 2 | 3 |
| Lemon Juice | 4 | 4 |
| Motor Oil | 0 | 4 |
| Canola Oil | 0 | 4 |
| Bacon Grease | 0 | 4 |
| Total | 11 | 35 |
| Water Beading | 4 | 1 |
| Oil Beading | 4 | 1 |

[a] % F in solution = 0.8%; applied 0.37 g/m²

TABLE 5

Stain resistance, water and oil repellency for granite[a]

| Food stains | Example 4 | Control |
| --- | --- | --- |
| Cola | 0 | 2 |
| Mustard | 0 | 3 |
| Ketchup | 0 | 1 |
| Grape juice | 3 | 4 |
| Italian dressing | 0 | 4 |
| Coffee | 2 | 3 |
| Lemon Juice | 0 | 2 |
| Motor Oil | 0 | 4 |
| Canola Oil | 0 | 4 |
| Bacon Grease | 0 | 4 |
| Total | 5 | 31 |
| Water Beading | 2 | 1 |
| Oil Beading | 3 | 1 |

[a] % F in solution = 0.8%; applied 0.36 g/m²

The data in Table 4 show that limestone treated with the composition of Example 4 exhibited improvement in stain resistance, oil repellency and water repellency, thus demonstrating efficacy as a hard porous surface protective sealer. The data in Table 5 show that granite treated with the composition of Example 4 also exhibited improvement in stain resistance, oil repellency and water repellency, thus demonstrating efficacy as a hard porous surface protective sealer.

Examples 1 to 4 were also tested for surface tension according to Test Method 3. Results are in Table 6. Examples 1 to 4 were added to semi-gloss latex paint in an amount of 0.03% by dry weight of the example in the wet paint and tested for contact angle using Test Method 4, and resistance to blocking using Test Method 2. Results are in Tables 7 and 8. Examples 3 and 4 were added to semi-gloss latex paint in an amount of 0.01% by dry weight of the example in the wet paint and tested for open time extension using Test 5. Results are in Table 9.

Example 5

Phosphorous pentoxide (0.99 g, 0.007 mol) was added to Compound 6 (5 g, 0.016 mol) at 85° C. and the mixture heated to 100° C. for 14 h. Isopropyl alcohol (5.31 mL) was added to the reaction mixture at 65° C., stirred for 1 h at 50° C., followed by the addition of DI water (6.72 mL). After 5 minutes, ammonia (1.05 mL, 30% aqueous solution, 0.027 mol) was added and the reaction was stirred for 1 h at 32° C. to provide phosphate 5 (r, q and j=1, $R_f$=—$C_4F_9$) wherein $^+X$ is $^+NH_4$. $^{31}P$ NMR of the product showed 46.3 mol % bis (fluoroalkyl)phosphate (x=2) and 31.8 mol % fluoroalkylphosphate (x=1). The resulting product was tested for surface tension, contact angle, resistance to blocking, and open time extension as described below with results in Tables 6 to 9.

Examples 6-8

Compounds 11, 7 and 12 (Table 1A) where treated in a similar manner as described in Example 5 to provide phosphate 6 (r, q and j=1, $R_f$=—$C_6F_{13}$), phosphate 7 (r=2, q and j=1, $R_f$=—$C_4F_9$) and phosphate 8 (r=2, q and j=1, $R_f$=—$C_6F_{13}$), respectively, wherein for each $^+X$ was $^+NH_4$. Phosphate 6 $^{31}P$ NMR showed 43.1 mol % bis(fluoroalkyl)phosphate (x=2) and 28.9 mol % fluoroalkylphosphate (x=1). Phosphate 7 $^{31}P$ NMR showed 54.1 mol % bis(fluoroalkyl) phosphate (x=2) and 25.9 mol % fluoroalkylphosphate (x=1). The resulting products were tested from surface tension, contact angle, resistance to blocking and open time extension as described below with results in Tables 6 to 9.

Example 9

Phosphorous pentoxide (0.96 g, 0.0068 mol) was added to compound 6 (5 g, 0.015 mol) at 85° C. and the mixture heated to 105° C. for 14 h. Ethylene glycol (12.5 g, EG) was added to the reaction mixture at 95° C., stirred for 25 min, followed by the addition of TERGITOL 15-S-9 surfactant, available from Sigma Aldrich, St. Louis, Mo., (1.16 g) at 86° C. After 10 min, ammonia (0.95 mL, 0.0153 mol, 30%) was added and the reaction was stirred for 10 min at 70° C. Water (30 mL) was added and the reaction was stirred at 70° C. for 1 h, and ammonia (1.6 mL 30%) was added to adjust the pH to 9.8 to provide phosphate 9 (r, q and j=1, $R_f$=—$C_4F_9$) wherein $^+X$ is $^+NH_4$. The resulting product was tested from surface tension, contact angle, resistance to blocking, and open time extension as described below with results in Tables 6 to 9.

Examples 10-12

Compounds 11, 7 and 12 where treated in a similar manner as described in Example 9 to provide phosphate 10 (r, q and j=1, $R_f$=—$C_6F_{13}$), phosphate 11 (r=2, q and j=1, $R_f$=—$C_4F_9$) and phosphate12 (r=2, q and j=1, $R_f$=—$C_6F_{13}$), respectively, wherein for each $^+X$ is $^+NH_4$. The resulting products were tested from surface tension, contact angle, resistance to blocking, and open time extension as described below with results in Tables 6 to 9.

Example Testing

The products of Examples 1-12 were added to deionized water based on solids content (weight %), and tested for surface tension according to Test Method 3. The resulting data is in Table 6.

The products of Examples 1-12 were added to semi-gloss latex paint in an amount of 0.03 weight % by dry weight of the composition of the invention in the wet paint. The contact angle was measured using Test Method 4 and the resulting data is in Table 7. Resistance to blocking was measured according to Test Method 2 with results in Table 8.

The products of Examples 1-12 were added to semi-gloss latex paint in an amount of 0.10 weight % by dry weight of the composition of the invention in the wet paint. Open time extension was measured using Test Method 5 with the resulting data in Table 9.

TABLE 6

| Surface Tension Data[a] in dyne/cm | | | | | | | | |
|---|---|---|---|---|---|---|---|---|
| Ex No. | 0.000% | 0.001% | 0.005% | 0.010% | 0.050% | 0.100% | 0.200% | 0.500% |
| 1 | 74.6 | 58.5 | 45.1 | 35.3 | 35.7 | 30.9 | 32.0 | 31.5 |
| 2 | 73.7 | 58.1 | 43.8 | 38.1 | 19.7 | 16.1 | 15.7 | 15.7 |
| 3 | 71.7 | 39.0 | 24.8 | 18.7 | 15.8 | 15.4 | 15.2 | 15.0 |
| 4 | 72.1 | 65.6 | 55.4 | 53.5 | 41.4 | 36.5 | 32.6 | 29.6 |
| 5 | 72.1 | 45.5 | 43.5 | 37.5 | 20.2 | 17.6 | 16.9 | 16.1 |
| 6 | 72.3 | 56.7 | 50.7 | 47.8 | 37.5 | 29.6 | 29.9 | 25.1 |
| 7 | 73.8 | 45.5 | 28.0 | 22.3 | 19.2 | 18.6 | 18.0 | 16.4 |
| 8 | 74.1 | 62.9 | 54.7 | 49.7 | 42.1 | 37.2 | 33.9 | 26.8 |
| 9 | 72.5 | 42.0 | 31.4 | 27.9 | 18.4 | 17.5 | 17.2 | 17.0 |
| 10 | 71.0 | 43.4 | 31.9 | 29.1 | 24.0 | 22.2 | 20.8 | 19.5 |
| 11 | 72.4 | 38.0 | 21.9 | 18.8 | 17.7 | 17.5 | 17.3 | 17.2 |
| 12 | 72.3 | 51.4 | 39.9 | 35.6 | 26.8 | 24.4 | 22.7 | 21.8 |

[a]The average of 10 replicates is reported. The standard deviation was <1 dyne/cm.

Normal surface tension of deionized water is about 72 dyne/cm (shown in the chart as 0% additive). According to the results from these tests, excellent surface tension reduction is seen from all examples of the present invention.

TABLE 7

| Advancing contact angle[a] semi-gloss latex paint | |
|---|---|
| Example | Hexadecane |
| Control | 28.1 |
| 1 | 76.8 |
| 2 | 68.4 |
| 3 | 56.8 |
| 4 | 67.5 |
| 5 | 74.2 |
| 6 | 73.2 |
| 7 | 57.4 |
| 8 | 63.7 |
| 9 | 74.0 |
| 10 | 62.0 |
| 11 | 64.2 |
| 12 | 53.6 |

[a]An average of 3 replicates of 7 mil drawdown samples.

Advancing hexadecane contact angle is correlated with oil repellency. The products of Examples 1-12 demonstrated excellent oil repellency by hexadecane (oil) contact angle data.

Comparative Example B

The procedure of Example 5 was employed, but using a perfluoroalkylethyl alcohol mixture of the formula $F(CF_2)_a CH_2CH_2OH$, wherein a ranged from 6 to 14, and was predominately 6, 8, and 10. The typical mixture was as follows: 27% to 37% of a=6, 28% to 32% of a=8, 14% to 20% of a=10, 8% to 13% of a=12, and 3% to 6% of a=14. The resulting product was tested for resistance to blocking and open time extension as described below. Results are in Tables 8 and 9.

Comparative Example C

The procedure of Example 9 was employed, but using a perfluoroalkylethyl alcohol mixture of the formula $F(CF_2)_b CH_2CH_2OH$, wherein b ranged from 6 to 14, and was predominately 6, 8, and 10. The typical mixture was as follows: 27% to 37% of b=6, 28% to 32% of b=8, 14% to 20% of b=10, 8% to 13% of b=12, and 3% to 6% of b=14. The resulting product was tested for resistance to blocking and open time extension as described below. Results are in Tables 8 and 9.

Example Testing

Examples 1 to 12 and Comparative Examples B and C were added to semi-gloss latex paint in an amount of 0.03 weight % by dry weight of the composition in the wet paint and tested for resistance to blocking using Test Method 2. Resulting data are in Table 8. Examples 1 to 12 and Comparative Examples B and C were added to semi-gloss latex paint in an amount of 0.10 weight % by dry weight of the composition in the wet paint and tested for open time extension using Test Method 5. Resulting data is in Table 9.

TABLE 8

Resistance to Blocking[a] in semi-gloss latex paint

| Examples | Blocking Rating |
| --- | --- |
| Untreated Control | 2.7 |
| 1 | 8.7 |
| 2 | 8.3 |
| 3 | 7.7 |
| 4 | 8.7 |
| 5 | 8.0 |
| 6 | 8.3 |
| 7 | 5.0 |
| 8 | 8.0 |
| 9 | 9.0 |
| 10 | 8.7 |
| 11 | 6.3 |
| 12 | 6.0 |
| Comparative B | 6.3 |
| Comparative C | 6.3 |

[a]An average of 3 replicates is reported.

According to the results in Table 8, excellent resistance to blocking was seen for products of Examples 1-12, and many of the Examples performed better than Comparative Examples B and C.

TABLE 9

Open-time extension in semi-gloss latex paint

| Example | Open Time Extension (min) | % Extension |
| --- | --- | --- |
| 3 | 3 | 12.0 |
| 4 | 6 | 26.1 |
| 5 | 7 | 25.9 |
| 6 | 6 | 23.1 |
| 7 | 4 | 14.8 |
| 8 | 7 | 25.9 |
| 9 | 5 | 18.5 |
| 10 | 4 | 12.5 |
| 11 | 4 | 11.4 |
| 12 | 4 | 13.3 |

According to the results in Table 9, excellent increased open-time extension values were seen for paints containing the products of Examples 3-12.

What is claimed is:

1. A method of providing water repellency, oil repellency and stain resistance to a substrate comprising contacting the substrate with a composition comprising one or more compounds of formula (I) or (II):

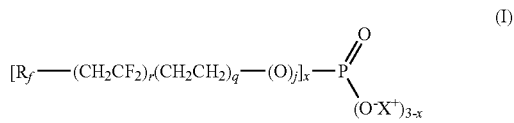

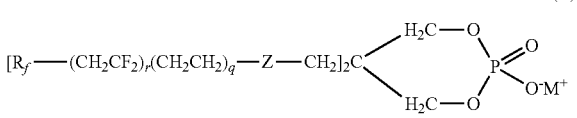

wherein
r and q are independently integers of 1 to 3;
$R_f$ is linear or branched chain perfluoroalkyl group having 1 to 6 carbon atoms;
j is an integer 0 or 1, or a mixture thereof,
x is 1 or 2,
Z is —O— or —S—,
X is hydrogen or M, and
M is an ammonium ion, an alkali metal ion, or an alkanolammonium ion.

2. The method of claim 1 wherein the contacting is by brush, spray, roller, doctor blade, wipe, dip, foam, liquid injection, immersion or casting.

3. The method of claim 1 wherein $R_f$ has 4 to 6 carbon atoms, and r, q and j are each 1.

4. The method of claim 1 wherein M is an ammonium or an alkanolammonium ion.

5. A substrate treated according to the method of claim 1.

6. A substrate to which has been applied a composition according to the method of claim 1.

7. The substrate of claim 6 comprising a fibrous substrate or a hard surface substrate.

8. The substrate of claim 7 which is a fiberous substrate selected from the group consisting of wood, paper or leather.

9. The substrate of claim 7 which is a hard surface substrate selected from the group consisting of stone, glass masonry, concrete, unglazed tile, brick, porous clay, granite, limestone, grout, mortar, marble, gypsum board, terrazzo, or composite materials.

* * * * *